(12) United States Patent
Szymiczek et al.

(10) Patent No.: US 10,835,692 B2
(45) Date of Patent: Nov. 17, 2020

(54) CHILDPROOF DISCHARGING DEVICE

(71) Applicant: APTAR RADOLFZELL GMBH, Radolfzell (DE)

(72) Inventors: Christoph Szymiczek, Singen (DE); Gerald Krampen, Radolfzell (DE); Juergen Greiner-Perth, Gottmadingen (DE)

(73) Assignee: APTAR RADOLFZELL GMBH, Radolfzell (DE)

( * ) Notice: Subject to any disclaimer, the term of this patent is extended or adjusted under 35 U.S.C. 154(b) by 1165 days.

(21) Appl. No.: 15/027,338

(22) PCT Filed: Sep. 11, 2014

(86) PCT No.: PCT/EP2014/069452
§ 371 (c)(1),
(2) Date: Apr. 5, 2016

(87) PCT Pub. No.: WO2015/051972
PCT Pub. Date: Apr. 16, 2015

(65) Prior Publication Data
US 2016/0243319 A1     Aug. 25, 2016

(30) Foreign Application Priority Data
Oct. 10, 2013   (DE) .................. 10 2013 220 492

(51) Int. Cl.
*A61M 11/00*    (2006.01)
*B05B 11/00*    (2006.01)
(Continued)

(52) U.S. Cl.
CPC .......... *A61M 11/007* (2014.02); *A61M 15/08* (2013.01); *B05B 11/0032* (2013.01);
(Continued)

(58) Field of Classification Search
CPC .. A61M 11/00; A61M 11/007; A61M 11/008; A61M 11/08; A61M 15/00;
(Continued)

(56) References Cited

U.S. PATENT DOCUMENTS 2,586,502 A    2/1952  Backus
3,422,996 A    1/1969  Lipman
(Continued)

FOREIGN PATENT DOCUMENTS

CA    2492255 A1    7/2006
CN    1407938 A     4/2003
(Continued)

OTHER PUBLICATIONS

Chinese Evaluation Report of Design Patent issued in Appln. No. ZL201430058495.4 dated Jul. 11, 2016 (20 pages).
(Continued)

*Primary Examiner* — Justine R Yu
*Assistant Examiner* — Matthew R Moon
(74) *Attorney, Agent, or Firm* — Flynn Thiel, P.C.

(57) ABSTRACT

A discharging device for a pharmaceutical liquid, dispenser including a housing, an applicator tip with a discharge opening and a protective cap. A locking tooth is provided on the protective cap and a counter tooth is provided on the applicator tip. The at least one locking tooth passes over the counter tooth when the protective cap is rotated relative to the applicator tip in a first direction, and the locking tooth and the counter tooth prevent rotation in a direction opposite the first direction. The protective cap and the applicator tip are adapted to each other such that the discharge opening contacts a lid region of the protective cap after the locking tooth has passed over the counter tooth, and the discharge opening can be closed in a sealed manner by the protective (Continued)

cap. The protective cap is deformable to disengage the locking tooth and the counter tooth.

22 Claims, 4 Drawing Sheets

(51) Int. Cl.
  *B65D 50/04* (2006.01)
  *A61M 15/08* (2006.01)
  *A61M 15/00* (2006.01)
(52) U.S. Cl.
  CPC ........ *B05B 11/3047* (2013.01); *B65D 50/046* (2013.01); *A61M 15/00* (2013.01); *A61M 15/009* (2013.01); *A61M 2205/276* (2013.01); *B65D 50/04* (2013.01)
(58) Field of Classification Search
  CPC ............ A61M 15/009; A61M 15/0091; A61M 15/08; A61M 2205/27; A61M 2205/276; A61M 11/006; A61M 15/0025; B05B 11/3047; B05B 11/00; B05B 11/0032; B65D 50/04; B65D 50/046; B67B 1/00
  See application file for complete search history.

(56) References Cited

U.S. PATENT DOCUMENTS

| | | | | |
|---|---|---|---|---|
| 3,770,153 | A * | 11/1973 | Gach | B65D 50/046 |
| | | | | 215/216 |
| 4,099,639 | A | 7/1978 | Boxer et al. | |
| 4,775,078 | A | 10/1988 | Schick et al. | |
| 4,801,093 | A | 1/1989 | Brunet et al. | |
| 5,687,863 | A | 11/1997 | Kusz | |
| 5,829,645 | A | 11/1998 | Hennemann | |
| 6,055,979 | A | 5/2000 | Fuchs | |
| 6,059,150 | A * | 5/2000 | Fuchs | A47K 5/16 |
| | | | | 222/190 |
| 6,059,151 | A * | 5/2000 | Fuchs | B05B 11/3004 |
| | | | | 222/321.6 |
| 6,065,648 | A * | 5/2000 | Tauber | B65D 47/242 |
| | | | | 222/153.14 |
| 6,105,801 | A * | 8/2000 | Minnette | B65D 1/023 |
| | | | | 215/216 |
| 6,276,568 | B1 * | 8/2001 | Brotspies | B05B 11/3052 |
| | | | | 222/321.6 |
| 6,357,615 | B1 | 3/2002 | Herr | |
| 6,412,659 | B1 * | 7/2002 | Kneer | B05B 11/3047 |
| | | | | 222/82 |
| 7,100,785 | B1 | 9/2006 | Suffa | |
| 7,306,116 | B2 * | 12/2007 | Fuchs | B05B 11/308 |
| | | | | 222/153.01 |
| 7,641,064 | B2 | 1/2010 | Robinson | |
| 8,079,483 | B2 | 12/2011 | Brozell et al. | |
| 8,210,376 | B2 | 7/2012 | Robinson | |
| 8,444,610 | B2 | 5/2013 | Grevin | |
| D738,214 | S | 9/2015 | Schwarz | |
| D738,215 | S | 9/2015 | Schwarz | |
| D739,237 | S | 9/2015 | Schwarz | |
| 2002/0166834 | A1 * | 11/2002 | Branson | B65D 50/046 |
| | | | | 215/216 |
| 2004/0222181 | A1 | 11/2004 | Biesecker et al. | |
| 2005/0173459 | A1 * | 8/2005 | Buxmann | B05B 11/0032 |
| | | | | 222/321.6 |
| 2006/0108312 | A1 | 5/2006 | Robinson | |
| 2006/0186141 | A1 * | 8/2006 | Greiner-Perth | B05B 11/3039 |
| | | | | 222/321.6 |
| 2006/0213860 | A1 | 9/2006 | Robinson | |
| 2007/0210027 | A1 * | 9/2007 | Abbott | B65D 50/045 |
| | | | | 215/214 |
| 2009/0140008 | A1 * | 6/2009 | Welp | B05B 11/0032 |
| | | | | 222/182 |
| 2010/0145287 | A1 * | 6/2010 | Grevin | A61F 9/0008 |
| | | | | 604/295 |
| 2010/0252581 | A1 * | 10/2010 | Greiner-Perth | B05B 11/3004 |
| | | | | 222/320 |
| 2010/0320168 | A1 | 12/2010 | Bull | |
| 2011/0089197 | A1 * | 4/2011 | Welp | A61M 15/08 |
| | | | | 222/321.2 |
| 2011/0303761 | A1 * | 12/2011 | Kohnle | A61M 11/005 |
| | | | | 239/102.1 |
| 2012/0126035 | A1 * | 5/2012 | Greiner-Perth | A61M 11/00 |
| | | | | 239/494 |
| 2013/0008981 | A1 * | 1/2013 | Bloc | B05B 11/3053 |
| | | | | 239/480 |
| 2015/0076174 | A1 * | 3/2015 | Mersmann | B05B 11/0027 |
| | | | | 222/153.13 |
| 2015/0272398 | A1 * | 10/2015 | Arminak | A47K 5/16 |
| | | | | 222/190 |
| 2015/0328651 | A1 * | 11/2015 | Hohmann | B05B 11/3053 |
| | | | | 239/480 |
| 2015/0335528 | A1 * | 11/2015 | Kim | B05B 11/3039 |
| | | | | 222/321.6 |

FOREIGN PATENT DOCUMENTS

| | | |
|---|---|---|
| CN | 1878703 A | 12/2006 |
| CN | 3609882D | 2/2007 |
| CN | 3636739D | 4/2007 |
| CN | 2898352 Y | 5/2007 |
| CN | 101039848 A | 9/2007 |
| CN | 101296850 A | 10/2008 |
| CN | 102196969 A | 9/2011 |
| CN | 202174028 U | 3/2012 |
| CN | 104340501 A | 2/2015 |
| DE | 93 12 423.6 | 3/1994 |
| DE | 197 40 686 A1 | 3/1999 |
| DE | 100 51 753 A1 | 5/2001 |
| DE | 696 18 425 T2 | 11/2002 |
| EM | 000136718-0004 | 5/2004 |
| EP | 0 799 646 A2 | 10/1997 |
| FR | 2 911 329 A1 | 7/2008 |
| GB | 689225 | 3/1953 |
| GB | 1 535 051 | 12/1978 |
| GB | 2 256 638 A | 12/1992 |
| JP | 11-208692 A | 8/1999 |
| JP | 2000-43909 A | 2/2000 |
| JP | 3915084 B2 | 2/2000 |
| JP | 2002-506409 A | 2/2002 |
| JP | D1188443 | 10/2003 |
| JP | D1233426 | 3/2005 |
| JP | D1233427 | 3/2005 |
| JP | D1310869 | 9/2007 |
| JP | 5037889 B2 | 4/2008 |
| KR | 30-0413151 | 5/2006 |
| KR | 30-0454861 | 7/2007 |
| WO | WO 98/55373 A2 | 12/1998 |
| WO | WO 2009/103947 A1 | 8/2009 |
| WO | WOD080384 | 8/2013 |
| WO | WO 2016/015353 A1 | 2/2016 |
| WO | WO 2016/015372 A1 | 2/2016 |

OTHER PUBLICATIONS

Office Action of the China Patent Office issued in Application No. 201480055678.8 with English translation dated Mar. 27, 2017 (23 pages).
European Patent Office Search Report issued in Application No. 16169459 with English translation of category of cited documents, dated Jan. 11, 2017 (10 pages).
International Search Report issued in Application No. PCT/EP2014/069452 with English translation, dated Nov. 18, 2014 (7 pages).
Written Opinion of International Searching Authority issued in Application No. PCT/EP2014/069452, dated Nov. 18, 2014 (5 pages).
Examination Report of European Patent Office issued in Application No. 16 16 9459 dated Aug. 26, 2016 with English translation of category of cited documents (8 pages).

(56) References Cited

OTHER PUBLICATIONS

Request for Invalidation with English Translation for corresponding Chinese Application No. 201480055678.8, dated Apr. 2, 2020 (35 pages).

Notice of Transferring Petitioner's Observation with English Translation for corresponding Chinese Application No. 201480055678.8, dated Apr. 17, 2020 (92 pages).

Office Action issued from Brazilian Patent Office with English Translation in corresponding Brazilian Patent Application No. 112016007599-4, dated May 4, 2020 (5 pages).

* cited by examiner

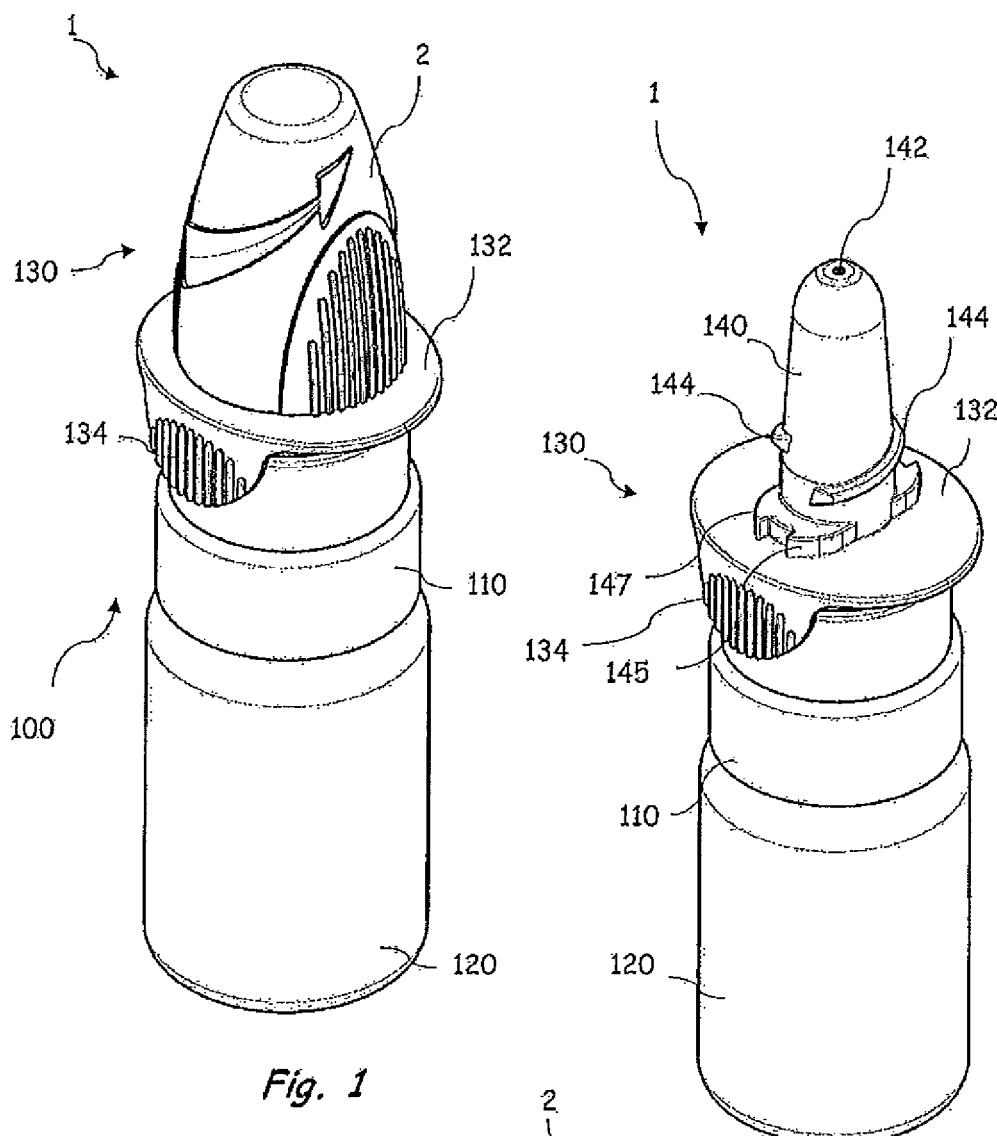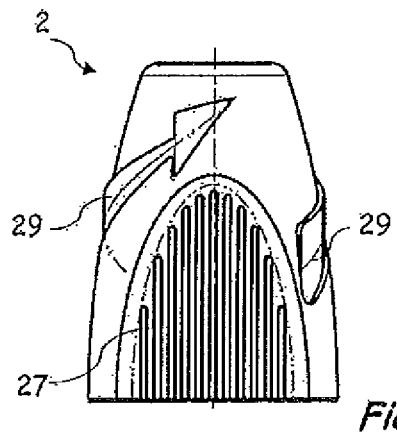

CHILDPROOF DISCHARGING DEVICE

SCOPE AND PRIOR ART

The invention relates to a discharging device for a dispenser for discharging pharmaceutical liquids, said discharging device including a housing having a coupling geometry for mounting on a liquid storage unit, an applicator tip having a discharge opening arranged on a distal end and a protective cap. The invention further relates to a dispenser for discharging pharmaceutical liquids, said dispenser including a liquid storage unit and a discharging device.

The liquids to be discharged by way of generic discharging devices and dispensers also include liquids the ingestion of which can be harmful if they are not medically induced. It is particularly problematic when children, for example out of curiosity or when playing, use pharmaceutical dispensers and in this case discharge and ingest liquid. Depending on the liquid, this can be linked to considerable risks to the health of a child.

In many countries of the world the given problem has resulted in legislative measures, according to which in the case of certain pharmaceutical liquids or active substances only dispensers which cannot normally be opened or actuated by children are allowed to be used as children do not comprehend the mode of implementation.

The handling of corresponding dispensers or discharging devices with a child lock is frequently arduous. Consequently, older persons in particular frequently take measures to circumvent the child lock. This then once again results in the risk that unobstructed access to the media stored in the manipulated dispensers is possible for children.

OBJECT AND ACHIEVEMENT

It is the object of the invention to develop generic discharging devices and dispensers further to the effect that with low structural expenditure an effective child lock and simple handling are achieved.

Said object is achieved by a generic discharging device, wherein the applicator tip comprises an external thread and the protective cap comprises an internal thread which interacts with the external thread of the applicator tip, at least one locking tooth is provided on the protective cap and at least one counter tooth is provided on the applicator tip, wherein when the protective cap is rotated relative to the applicator tip in a first direction for screwing on the protective cap, the at least one locking tooth overruns the at least one counter tooth and, after overrunning, the at least one locking tooth and the at least one counter tooth prevent a rotation in the direction opposite to the first direction for unscrewing the protective cap, the protective cap and the applicator tip are matched to one another in such a manner that, after overrunning the at least one counter tooth, the discharge opening is in contact with a cover region of the protective cap and the discharge opening is closable in a sealed manner by the protective cap, and the protective cap is resiliently deformable at least in portions in order to disengage the at least one locking tooth and the at least one counter tooth as a result of resiliently deforming the protective cap.

To remove the protective cap, in this case lateral deforming forces and torque have to be applied simultaneously. These types of mechanisms are also designated as squeeze and turn closures. Studies have shown that a combination of force or movement of this type is difficult for children, but intuitively possible for adults.

In one development, the external thread provided on the applicator tip extends over an entire length of the applicator tip. In other developments, the threads are developed in such a manner that a rotating movement when screwing-on is effected over an angle of less than 360°, preferably less than 180°. This ensures that the rotating movement is carried out until the counter tooth is overrun and consequently until the secured end position is reached, and the user does not abort the operation prematurely on account of tiredness. The thread portions, in this case, are arranged in advantageous developments such that a region surrounding the discharge opening is thread-free. As a result, use without any loss of comfort or convenience is ensured, in particular even when an applicator tip is developed as a nose olive.

When screwing on the protective cap, the at least one locking tooth of the protective cap overruns the at least one counter tooth of the applicator tip. After overrunning, the at least one locking tooth and at least one counter tooth prevent a movement in an opposite direction. The teeth are preferably developed in such a manner that overrunning is possible at low forces, a movement in the opposite direction, however, is opposed by higher forces.

The protective cap is resiliently deformable at least in portions. The protective cap is produced for this purpose in advantageous developments from a resiliently deformable plastics material, for example from polypropylene. The deforming, in this case, is utilized both when overrunning and when releasing the engagement. In one development it is provided that the locking tooth of the protective cap is itself resiliently deformed. As an alternative to this or in addition to it, in other developments a region supporting the locking tooth is deformed. At the end of the movement for overrunning the at least one counter tooth, the protective cap and/or the locking tooth springs back into its original form. The change is preferably connected to a popping noise which signals to the user that the secured end position has been reached.

In advantageous developments, the protective cap is in one part. In the sense of the present invention, in one part is also to be understood, where applicable, as a protective cap which is fixedly assembled from several individual parts, e.g. by means of screw-connecting, bonding, welding or any other type of connection. The protective cap is preferably produced as a single or multiple component injection molding part.

The protective cap is matched to the applicator tip in such a manner that the protective cap is screwable sufficiently far onto the applicator tip in order to close the discharge opening in a sealed manner by the protective cap. In one development, the protective cap comprises a sealing element on a cover region, the protective cap being in contact with the discharge opening by means of the sealing element. In advantageous developments, a cover region of the protective cap abutting against the discharge opening is resiliently deformed during the screwing-on procedure and when overrunning the counter tooth. The cover region, in this case, abuts against the applicator tip under the influence of the resilient resetting forces. In advantageous developments, an inside surface of the protective cap abuts against the discharge opening in the screwed-on state and closes said opening as a result. For an increased pressing force, in one development the cover region comprises a curvature in the direction of the interior of the protective cap. In other developments, in the region the protective cap comprises a continuation which engages in the discharge opening when the protective cap is screwed on.

In one development, two diametrically arranged counter teeth are provided on the on the applicator tip and two diametrically arranged locking teeth which interact therewith are provided on the protective cap. This makes secure locking possible. For a user to deform the protective cap for removing the protective cap, in advantageous developments said protective cap, in this case, comprises two force application surfaces which are arranged between the locking teeth. In one development the force application surfaces comprise a surface design which allows for simple gripping for applying the necessary deforming and rotating forces.

In one development, it is provided that the at least one locking tooth, preferably two diametrically arranged locking teeth, protrudes/protrude from a free end facing the housing and is insertable into a recess or are insertable into two complementary recesses on which (in each case) a counter tooth is provided. In other developments it is provided that the at least one counter tooth, preferably two diametrically arranged counter teeth, protrudes/protrude from a surface facing the protective cap and is insertable into a recess or are insertable into two complementary recesses on which (in each case) a locking tooth is provided. In an advantageous development it is provided that the at least one locking tooth and the at least one counter tooth protrude in each case in the radial direction with opposite orientation. Preferably, the at least one locking tooth protrudes inward from an inner lateral surface of the protective cap and interacts with a counter tooth which protrudes radially outward.

In a further development, at least one stop, by means of which the rotation of the protective cap relative to the applicator tip is defined in the first direction for screwing on the protective cap after overrunning the at least one counter tooth, is provided on the applicator tip. For the user, in this case, the achieving of the secured end position is haptically perceptible on account of the increased resistance force. In advantageous developments, the at least one locking tooth of the protective cap reaches the stop before a free end of the protective cap bears on a counter surface of the discharging device. As a result, even in the case of large tolerances it is ensured when screwing-on that the secured end position is reached and the screwing operation is not aborted on account of the components tilting or the like. The at least one locking tooth of the protective cap is preferably developed in an asymmetric manner and comprises a first flank which interacts with the counter tooth and a second flank which is at a spacing thereto in the circumferential direction and interacts with the stop of the applicator tip. The second flank is preferably developed so as to be shorter than the first flank.

In an advantageous development, the protective cap comprises two coaxially aligned sleeve portions, wherein the internal thread is arranged on an inner sleeve portion and the at least one locking tooth is arranged on an outer sleeve portion. The outer sleeve portion, in this case, is developable in such a manner that deforming as a result of applying a suitably chosen force for an ergonomic operation and childproof mounting are possible. Simultaneously deforming the internal thread when applying the force is prevented or reduced to an acceptable amount for the operation as a result of mounting the internal thread on a separate sleeve portion.

It is provided in a further development that the at least one locking tooth is arranged on an end of the outer sleeve portion located opposite the cover region and the internal thread is arranged on an end of the inner sleeve portion located opposite the cover region. Fastening on the applicator tip is consequently effected in a region that is remote from the discharge opening.

In an advantageous development, on an outer lateral surface the protective cap comprises a visually and/or haptically perceptible marking which describes an operation for screwing on and/or unscrewing the protective cap in the form of a symbol and/or as text. In this case, it has been shown that children, as a rule, are also not able to interpret symbolic representations of necessary operating steps for removing the protective cap. Adults, in contrast, are as a rule easily able to determine them independent of language. The marking is effected in one development in color, an imprint or the like being applied. In other developments, a marking is realized by means of multi-component injection molding.

In advantageous developments a marking is effected by means of a relief. In one development, the outer lateral surface is developed so as to converge elliptically, the relief-like marking being provided on a surface with a straight circular cylindrical envelope curve. As a result, an aesthetically pleasing and production-optimized relief is created. The marking rests on an "own" surface which, when viewed in the radial direction, is partially behind and partially in front of the outer lateral surface. As a result, good visual perceptibility is produced without additional color development on account of a light/shadow effect.

The liquid storage unit is developed in one development as a so-called squeeze bottle, discharging the stored liquid being achieved as a result of applying a lateral deforming force.

It is provided in advantageous developments that the discharging device includes an actuation unit which is displaceable in an axial direction in relation to the housing and has a finger support surface, wherein liquid originating from the liquid storage unit can be output through the discharge opening into a surrounding atmosphere by means of the actuation unit. In the case of a particularly preferred development of the discharging device, it is provided that said discharging device has a piston pump with a pump cylinder and a pump piston which together define a pump chamber and which, by applying force onto the actuation unit, are displaceable for the purposes of discharging liquid while at the same time reducing a volume of the pump chamber from an initial relative position up to an end relative position. A return flow channel, which connects the pump chamber to the liquid storage unit once an intermediate relative position is exceeded, is provided in one development in this case. In the case of such a development, the actuation of the actuation unit is not impeded by means of the protective cap. On account of the sealingly fitted protective cap, however, no liquid is discharged. In another development, the piston pump does not have a return or overflow channel. The liquid in the pump chamber can consequently not leak into the liquid storage unit. The liquid present in the pump chamber consequently opposes a movement of the actuation unit for the purposes of discharging the liquid. The protective cap, in this case, blocks a movement of the actuation unit not in a mechanical manner, but on account of the sealing of the outlet opening in a hydraulic manner. The applicator tip, in this case, is preferably connected fixed in position to the actuation unit. A discharge opening, which is displaceable together with the actuation unit in relation to the housing, is consequently provided in the case of a discharging device of this type. The protective cap prevents a discharge when actuated.

In one development, the actuation unit is mounted in the housing so as to be rotatable and displaceable in the axial direction. In order to apply a counter force for screwing on or unscrewing the protective cap, the user, in this case, grips the actuation unit with his second hand. In advantageous developments, the actuation unit is mounted in the housing in contrast so as to be non-rotatable and displaceable in the axial direction. As a result, it is possible for the user to grip the housing or the actuation unit or—in the case of non-rotatable coupling with the housing—the liquid storage unit. As a result, particularly ergonomically favorable handling is achieved.

The force application surfaces of the protective cap, on which a lateral deforming force and torque are applied for removing the protective cap, and the finger support surface are preferably developed in such a manner that, with the protective cap fitted in position, the force application surfaces enclose an angle of approximately 90° with the finger support surface. This allows for good force application, it being possible for a hand of a user, where applicable, also to be guided on the finger support surface.

In order to apply a counter force, in advantageous developments the actuation unit and/or the housing comprise at least one grip surface which is preferably substantially in a plane with the at least one counter tooth provided on the applicator tip. Two diametrically arranged grip surfaces which are arranged offset by 90° to the force application surfaces of the protective cap are preferably provided. This allows for particularly ergonomically favorable handling. The grip surfaces preferably enclose an angle of approximately 90° with a plane of the finger support surface.

The discharging device can be developed for different types of dispensers, for example for dispensers for oral delivery of liquid or for topical delivery of liquids. The development of the discharging device for a nasal dispenser for nasal delivery of liquids is deemed as particularly expedient. Such a discharging device preferably has an applicator tip which is developed as a nose olive, on the distal end of which is provided the discharge opening. The nose olive is preferably mounted fixed in position with regard to the actuating handle.

The object is further achieved by a dispenser for discharging pharmaceutical liquids, said dispenser including a liquid storage unit and a discharging device which is connected thereto and has the above-described features. Dispensers according to the invention are expedient in particular in the case of pharmaceutical liquids, the ingesting of which is accompanied by considerable risk. Analgesics, for example, are one of these. The use of a dispenser according to the invention with pharmaceutical liquids/formulations with nasal mucous membrane decongestants such as, for example, imidazoline is also expedient.

BRIEF DESCRIPTION OF THE DRAWINGS

Further aspects and advantages of the invention are also produced apart from the claims from the following description of preferred exemplary embodiments of the invention which are explained below by way of the figures, in which:

FIG. 1 shows a perspective representation of a dispenser with a discharging device according to a first development of the invention with a protective cap fitted in position, FIG. 2 shows a perspective representation of the dispenser according to FIG. 1 without the protective cap, FIG. 3 shows a side view of the protective cap for the dispenser according to FIG. 1, FIG. 4 shows a sectioned representation of the protective cap according to FIG. 3.

DETAILED DESCRIPTION OF THE EXEMPLARY EMBODIMENTS

Figure 5:
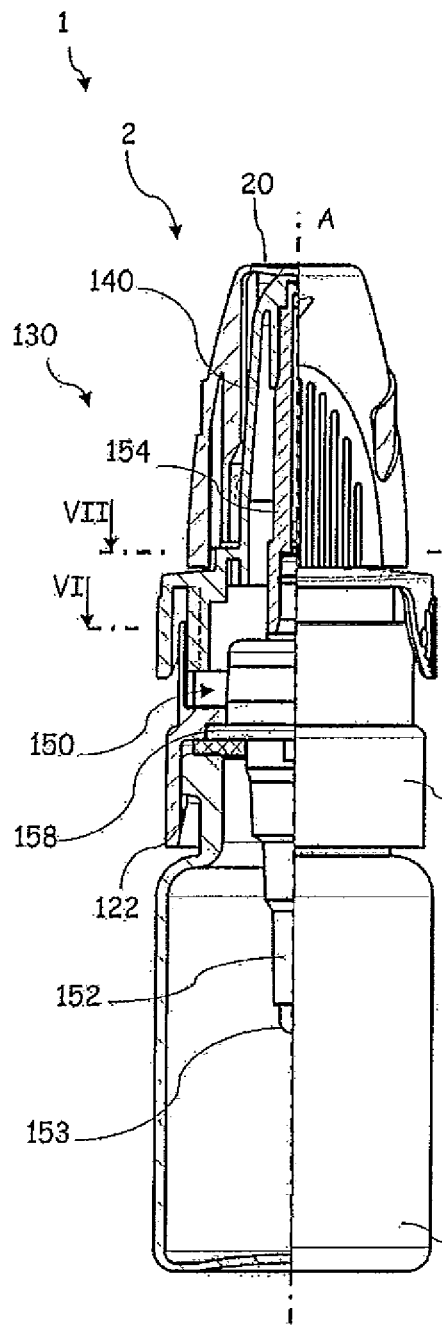
FIG. 5 shows a half-section of the dispenser according to FIG. 1.
Figure 6:
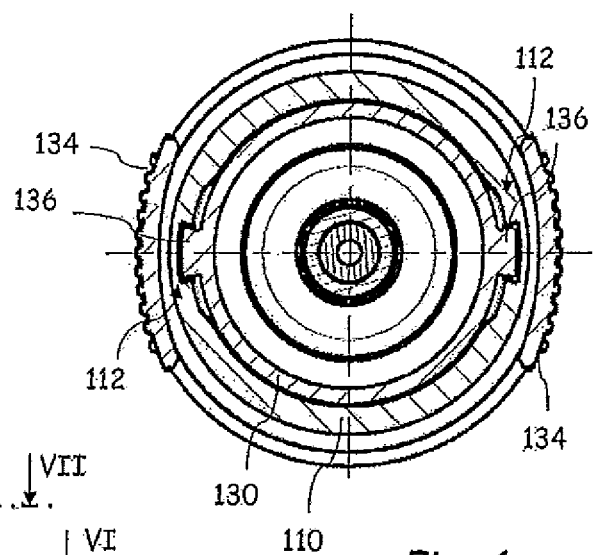
FIG. 6 shows a sectioned representation of the dispenser according to FIG. 1 along a cutting plane VI-VI according to FIG. 5.
Figure 7:
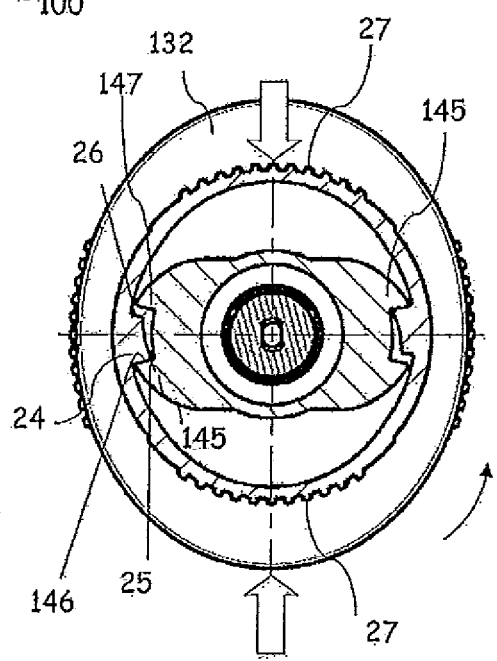
FIG. 7 shows a sectioned representation of the dispenser according to FIG. 1 along a cutting plane VII-VII according to FIG. 5.

FIGS. 1 to 7 show a dispenser 1 with a discharging device 100 according to a first development of the invention. In this case, FIGS. 1 and 2 show perspective representations of the dispenser 1 with a protective cap 2 fitted in position or without a protective cap. FIGS. 3 and 4 show a side view and a sectioned representation of the protective cap 2. FIG. 5 shows a half-section view of the dispenser 100 and FIGS. 6 and 7 show sectioned top views of the dispenser 100 along cutting planes VI-VI or VII-VII according to FIG. 5.

The discharging device 100 shown in FIGS. 1, 2 and 5 to 7 has a housing 110 to which an external liquid storage unit 120 is coupled by means of a snap-type connection 122. On the side of the housing 110 remote from the liquid storage unit 120, the discharging device 100 shown comprises an actuation unit 130 which has a finger support surface 132. An applicator tip 140, which is developed as a nose olive and on the distal end of which a discharge opening 142 is arranged, is provided on said actuation unit 130. The actuation unit 130 is displaceable in an axial direction A in relation to the housing 110, a displacement of the actuation unit 130 in the direction toward the housing 110 being necessary for the purposes of discharging liquid.

A pump device 150, the inlet channel 152 of which projects into the liquid storage unit 120, is provided inside the housing 110. A riser tube 153, which is shown in shortened form in the figures, is provided for sucking in liquid. The outlet channel 154 of the pump device 150 is fastened on the inside surface of the applicator tip 140. The main body 158 of the pump device 150 is positionally fixed between the liquid storage unit 120 and the housing 110. When the actuation unit 130 is displaced with the applicator tip 140 in the direction toward the liquid storage unit 120, the movement is transmitted to the outlet channel 154 of the pump device 150, as a result of which liquid is conveyed to the discharge opening 142. This is obtained by means of an internal piston pump (not shown) inside the pump device 150. As an alternative to this, it could also be provided that the liquid is present in a pressurized manner in the liquid storage unit 120 and that the discharge is controlled by a switchable valve device instead of the pump device.

The protective cap 2, which can be fastened on the applicator tip 140, is provided in order to prevent unwanted liquid discharge, for example caused by playing children. The protective cap 2 shown comprises a cover region 20 which, in the closed state as can be seen in FIG. 3, abuts against the discharge opening 142 and closes said opening in a sealing manner. The protective cap 2 further comprises two coaxially aligned sleeve portions 21, 22 which protrude from the cover region 20. In the exemplary embodiment shown, both sleeve portions 21, 22 have a rotationally symmetrical basic form. However, developments where the outer sleeve portion 22 is not developed in a rotationally symmetrical manner are also conceivable.

The coupling geometry between the protective cap 2 and the applicator tip 140 is developed as a so-called "lateral push-twist closure" or as a "squeeze and turn closure". To open the closure and remove the protective cap 2, it is necessary to apply a deforming force with a force component in the radial direction and torque at the same time at specific regions of the protective cap 2.

The protective cap 2 and the applicator tip 140 comprise complementary threads for this purpose. In the exemplary embodiment shown, an external thread 144 including two right-handed thread portions is provided on an outside lateral surface of the applicator tip 140. The thread portions of the external thread 144 are arranged on the applicator tip 140 in a point-symmetrical manner with respect to one another and extend in each case over an angle of less than 180°. A complementary internal thread 23 with two thread portions is provided on the protective cap 2, more precisely on the inner sleeve portion 22, such that it is possible to mount the protective cap 2 in two alignments of the protective cap 2 twisted by 180° in the axial direction.

The protective cap 2 further comprises two locking teeth 24 which are offset by 180° and interact with counter teeth 145 on the applicator tip 140, as can be seen the best in FIG. 7. The locking teeth 24 are arranged on an end of the outer sleeve portion 21 located opposite the cover region 20. In the end position secured against unscrewing, a flank 25 of the locking teeth 24 abuts against a counter flank 146 of the counter tooth 145 as shown in FIG. 7 such that rotating the protective cap 2 relative to the applicator tip 140 in an anticlockwise manner to open the closure and remove the protective cap 2 is blocked. As a result of applying a deforming force F, which is indicated schematically by arrows, on two force application surfaces 27 which are arranged offset to the locking teeth 24 in each case by 90', the protective cap 2 is deformed and the locking tooth 24 is movable out of engagement with the counter tooth 145. For this purpose, the user is able to grip the actuation unit 130 in an ergonomically favorable manner at two diametrically arranged grip surfaces 134. When the protective cap 2 is fitted in the secured end position, as shown, the grip surfaces 134 are offset by 90° to the force application surfaces 27. This allows for ergonomically favorable force application.

Two stops 147, by means of which a rotation of the protective cap 2 relative to the applicator tip 140 is defined for screwing on the protective cap 2 after overrunning the counter teeth 145, are further provided on the applicator tip 140. As can be seen in FIG. 7, the two locking teeth 24 of the protective cap 2 are developed in each case in an asymmetric manner and in each case comprise the first flank 25 which interacts with the counter tooth 145 and a second flank 26 which is at a spacing thereto in the circumferential direction and interacts with the stop 147. The second flank 26, in this case, is shorter than the first flank 25. The flanks 25, 26 are connected by means of a front flank which is slightly curved in the exemplary embodiment shown. The stops 147 are developed in each case in a mirror-symmetrical manner to the counter teeth 145.

As can be seen in FIG. 4, the thread portions of the internal thread 23 end at the locking teeth 24 when viewed in the circumferential direction.

As can also be seen in FIG. 4, the outer lateral surface of the outer sleeve portion 23 is developed so as to converge elliptically. The outer lateral surface comprises a visually and/or haptically perceptible marking 29 which describes an operation for screwing on and/or unscrewing the protective cap 2 in the form of a symbol. The marking 29 is provided in the exemplary embodiment shown as a relief on a surface with a straight circular cylindrical envelope curve. The surface of the marking 29, in this case, protrudes on an end of the outer lateral surface which faces the cover region 20, whereas at the oppositely situated end it forms an indentation in the lateral surface. And at the To discharge the liquid after removing the protective cap 2, a force has to be applied in the axial direction A on the finger support surface 132 in order to displace the actuation unit 130 in relation to the housing 110.

In the exemplary embodiment shown in FIGS. 1 to 5, the actuation unit 130 is mounted in the housing 110 so as to be non-rotatable and displaceable in the axial direction A. In the exemplary embodiment shown, a sleeve-shaped portion of the actuation unit 130 is guided in a portion of the housing 110 which is developed in a corresponding manner as a bushing. For non-rotatable guiding, the portion of the housing 110 developed as a bushing comprises two diametrically arranged grooves 112 in which two guide ribs 136 which are provided on the sleeve-shaped portion of the actuation unit 130 are guided.

Figures 8, 9:
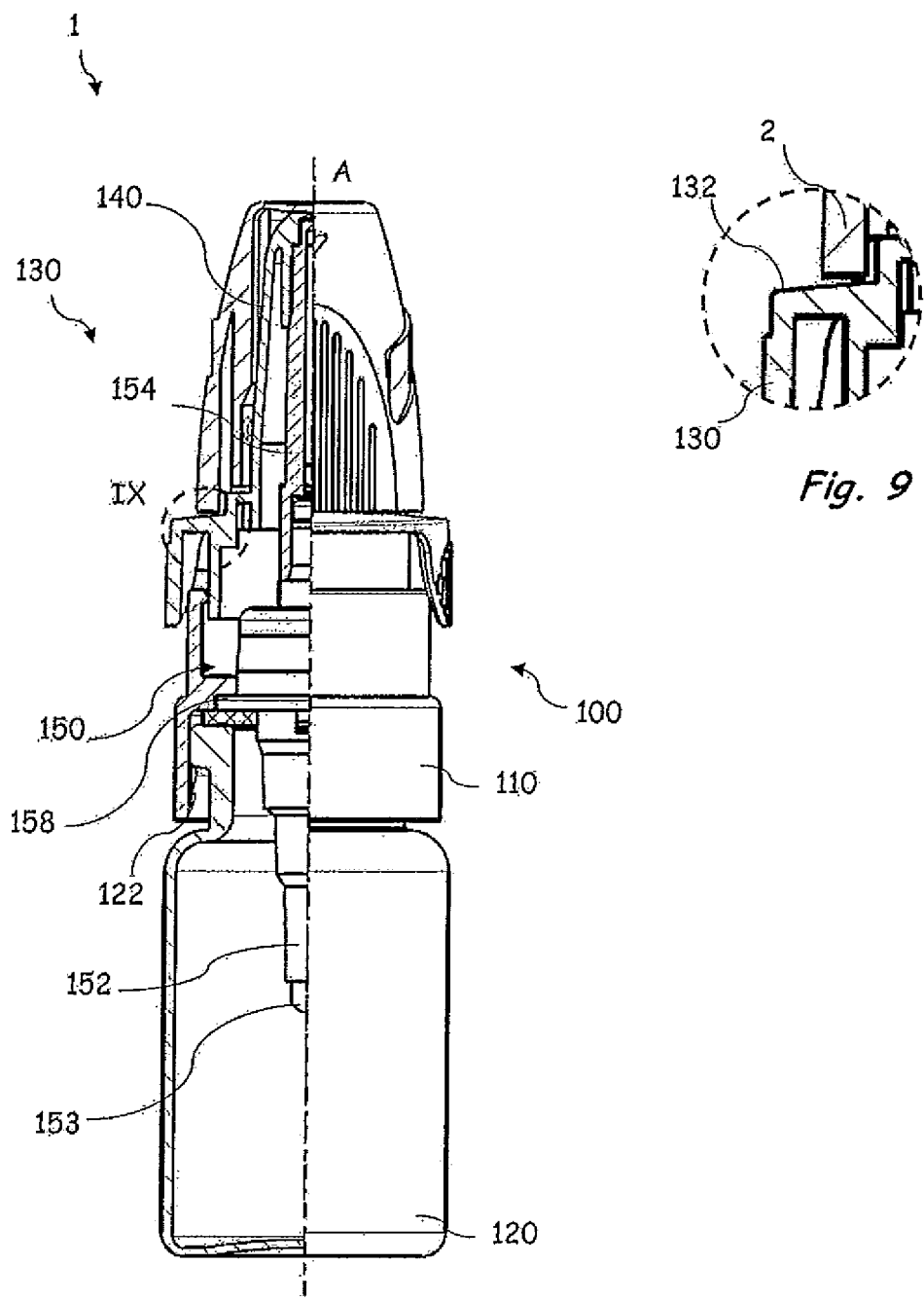
FIG. 8 shows a half-section of a dispenser with a discharging device similar to FIG. 5.
FIG. 9 shows a detail IX of the dispenser according to FIG. 8.

FIG. 8 shows a half-section of a second development of a dispenser 1 with a discharging device 100. The dispenser 1 and the discharging device correspond substantially to the dispenser 1 or the discharging devices according to FIGS. 1 to 7. Uniform reference symbols are used for identical components and there is no need for another description.

In contrast to the dispenser according to FIGS. 1 to 7, the actuation unit 130 is mounted in the housing 110 so as to be rotatable and displaceable in the axial direction A, a sleeve-shaped portion of the actuation unit 130 also being guided in a portion of the housing 110 which is developed in a corresponding manner as a bushing for this purpose.

FIG. 9 shows a detail IX according to FIG. 8. As described above, a stop 147 shown in FIG. 7 prevents further rotation after overrunning the counter tooth 145. As can be seen in FIG. 9, in this case the components are matched to one another in such a manner that, after overrunning the counter tooth 145, a free end of the protective cap 2 does not yet abut against the finger support surface 132 of the actuation unit 130. A corresponding development is also advantageous in the case of the discharging device 100 according to FIGS. 1 to 7.

Figure 10:
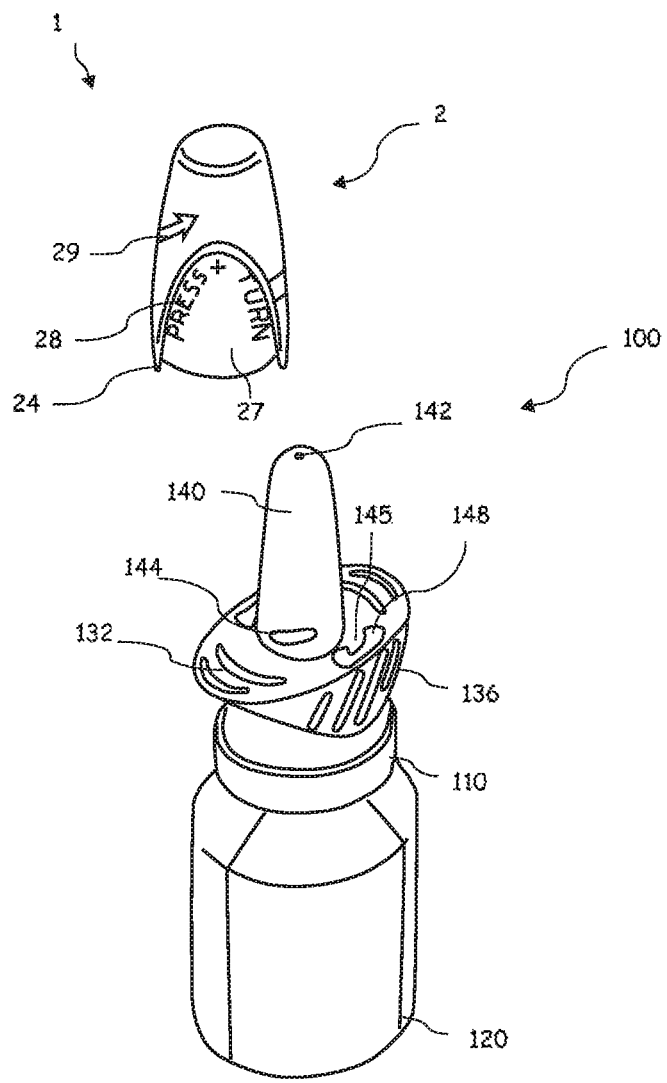
FIG. 10 shows a perspective representation of a dispenser with a discharging device.

FIG. 10 shows in a schematic manner a further development of a dispenser 1 including a discharging device 100 showing an assumed protective cap 2 and a liquid storage unit 120. The components of said development also correspond substantially to the components according to FIGS. 1 to 7 and uniform reference symbols are used for identical or similar components.

The discharging device 100 includes a housing 110 and an applicator tip 140 having a discharge opening 142 arranged on a distal end. The protective cap 2 serves for sealingly closing the discharge opening. The protective cap 2 comprises a non-visible internal thread which interacts with an external thread 144 on the applicator tip 140. Two axially protruding locking teeth 24, which interact with counter teeth 145 which are arranged fixed in position on the applicator tip 140, are provided additionally on the protective cap 2 for a child lock. The counter teeth 145 are provided in each case in a recess 148 on a surface which faces the protective cap 2. The locking teeth 24 overrun the counter teeth 145 thereby deforming the protective cap 2 and/or the locking teeth 24 and after overrunning the counter teeth 145 spring back into their original form. The locking teeth 24 and the counter teeth 145 then abut against one another and prevent a rotational movement of the protective cap 2 relative to the applicator tip 140 and consequently a removal of the protective cap 2.

In order to remove the protective cap 2, a lateral deforming force has to be applied on two force application surfaces 27 which are arranged between the locking teeth. The necessary movement is indicated by markings 28, 29 on the protective cap 2. A marking 28 which describes an operation for screwing on and/or unscrewing the protective cap as text and a marking 29 which describes an operation in the form of symbols are both provided in this case.

The force application surfaces 27, with the protective cap 2 fitted in position, are arranged offset by approximately 90° to two grip surfaces 134 assigned to the applicator tip 140. The grip surfaces 134 are perpendicular to the surface facing the protective cap 2.

The applicator tip 140 is connected rigidly to the housing 110 in one development. In other developments, the applicator tip 140 is mounted as above fixed in position on an actuation unit 130, the surface facing the protective cap 2 serving as the finger support surface 132 of the actuation unit.

The invention claimed is:

1. A discharging device for a dispenser for discharging pharmaceutical liquids, said discharging device including:
   a housing having a coupling geometry for mounting on a liquid storage unit,
   an applicator tip having a discharge opening arranged on a distal end, and
   a protective cap,
   wherein
   the discharging device includes an actuation unit including the applicator tip which is displaceable in an axial direction in relation to the housing and has a finger support surface adapted to receive a user's finger, wherein liquid originating from the liquid storage unit can be output through the discharge opening into a surrounding atmosphere by the actuation unit,
   the applicator tip comprises an external thread and the protective cap comprises an internal thread which interacts with the external thread of the applicator tip,
   at least one locking tooth is provided on the protective cap and at least one counter tooth is provided on an upper side of the finger support surface of the applicator tip, wherein when the protective cap is rotated relative to the applicator tip in a first direction for screwing on the protective cap, the at least one locking tooth overruns the at least one counter tooth and, after overrunning, the at least one locking tooth and the at least one counter tooth prevent a rotation in a second direction opposite to the first direction for unscrewing the protective cap, and the protective cap is resiliently deformable at least in portions in order to disengage the at least one locking tooth and the at least one counter tooth as a result of resiliently deforming the protective cap.

2. The discharging device as claimed in claim 1, wherein the protective cap and the applicator tip are matched to one another in such a manner that, after overrunning the at least one counter tooth, the discharge opening is in contact with a cover region of the protective cap and the discharge opening is closable in a sealed manner by the protective cap.

3. The discharging device as claimed in claim 1, wherein the at least one counter tooth comprises two diametrically arranged counter teeth provided on the applicator tip and the at least one locking tooth comprises two diametrically arranged locking teeth provided on the protective cap that interact with the arranged two diametrically counter teeth, wherein the protective cap comprises two force application surfaces which are arranged between the locking teeth.

4. The discharging device as claimed in claim 3, wherein with the protective cap secured to the applicator tip, the force application surfaces of the protective cap define an angle of approximately 90° with the finger support surface.

5. The discharging device as claimed in claim 3, wherein the actuation unit and/or the housing comprises two grip surfaces offset by approximately 90° relative to the force application surfaces of the protective cap.

6. The discharging device as claimed in claim 1, wherein the at least one locking tooth and the at least one counter tooth protrude in each case in a radial direction with opposite orientation.

7. The discharging device as claimed in claim 1, wherein at least one stop, by which the rotation of the protective cap relative to the applicator tip is defined in the first direction for screwing on the protective cap after overrunning the at least one counter tooth, is provided on the applicator tip, wherein the at least one locking tooth is configured in an asymmetric manner and comprises a first flank which interacts with the counter tooth and a second flank spaced therefrom in a circumferential direction and interacting with the stop of the applicator tip.

8. The discharging device as claimed in claim 1, wherein the protective cap comprises two coaxially aligned sleeve portions, wherein the internal thread is arranged on an inner sleeve portion and the at least one locking tooth is arranged on an outer sleeve portion.

9. The discharging device as claimed in claim 2, wherein the protective cap comprises two coaxially aligned sleeve portions, wherein the internal thread is arranged on an inner sleeve portion and the at least one locking tooth is arranged on an outer sleeve portion, and wherein the at least one locking tooth is arranged on an end of the outer sleeve portion located opposite the cover region and the internal thread is arranged on an end of the inner sleeve portion located opposite the cover region.

10. The discharging device as claimed in claim 1, wherein on an outer lateral surface the protective cap comprises a visually and/or haptically perceptible marking which describes an operation for screwing on and/or unscrewing the protective cap in the form of a symbol and/or as text.

11. The discharging device as claimed in claim 10, wherein the marking is configured as a relief.

12. The discharging device as claimed in claim 1, wherein the actuation unit is mounted on the housing so as to be non-rotatable and displaceable in the axial direction.

13. The discharging device as claimed in claim 1, wherein the discharging device is configured as a nasal dispenser for nasal delivery of a liquid medium and the applicator tip is configured as a nose olive with an elongated shape.

14. A dispenser for discharging pharmaceutical liquids, said dispenser including a liquid storage unit and a discharging device as claimed in claim 1 connected thereto.

15. The discharging device as claimed in claim 1, wherein the external thread extends over an angle of less than 180°.

16. The discharging device as claimed in claim 1, wherein the at least one locking tooth comprises a pair of opposite inwardly radially projecting locking teeth, and including a pair of opposite outwardly radially extending receptacle members provided on the upper side of the finger support surface of the applicator tip, each of the receptacle members having an outwardly facing U-shaped receptacle for receiving one of the locking teeth therein when the protective cap is in a locked position, an outer surface of the receptacle members defining the at least one counter tooth such that each of the locking teeth have to overrun the outer surface of the receptacle members and be received within the U-shaped receptacle for locking the cap in the locked position, each of the outwardly facing U-shaped receptacles having an inner surface thereof defining a stop by which the rotation of the protective cap relative to the applicator tip in the first direction for screwing on the protective cap after overrunning the at least one counter tooth is stopped.

17. A discharging device for a dispenser for discharging pharmaceutical liquids, said discharging device including:
   a housing having a coupling geometry for mounting on a liquid storage unit,
   an applicator tip having a discharge opening arranged on a distal end, and
   a protective cap,
   wherein
   the discharging device includes an actuation unit including the applicator tip which is displaceable in an axial direction in relation to the housing and has a finger support surface adapted to receive a user's finger, wherein liquid originating from the liquid storage unit can be output through the discharge opening into a surrounding atmosphere by the actuation unit,
   the actuation unit is mounted on the housing so as to be non-rotatable and displaceable in the axial direction, the applicator tip comprises an external thread and the protective cap comprises an internal thread which interacts with the external thread of the applicator tip, at least one locking tooth is provided on the protective cap and at least one counter tooth is provided on an upper side of the finger support surface of the applicator tip, wherein when the protective cap is rotated relative to the applicator tip in a first direction for screwing on the protective cap, the at least one locking tooth overruns the at least one counter tooth and, after overrunning, the at least one locking tooth and the at least one counter tooth prevent a rotation in a direction opposite to the first direction for unscrewing the protective cap, and
   the protective cap is resiliently deformable at least in portions in order to disengage the at least one locking tooth and the at least one counter tooth as a result of resiliently deforming the protective cap.

18. The discharging device as claimed in claim 17, wherein the external thread extends over an angle of less than 180°.

19. The discharging device as claimed in claim 17, wherein the at least one locking tooth comprises a pair of opposite inwardly radially projecting locking teeth, and including a pair of opposite outwardly radially extending receptacle members provided on the upper side of the finger support surface of the applicator tip, each of the receptacle members having an outwardly facing U-shaped receptacle for receiving one of the locking teeth therein when the protective cap is in a locked position, an outer surface of the receptacle members defining the at least one counter tooth such that each of the locking teeth have to overrun the outer surface of the receptacle members and be received within the U-shaped receptacle for locking the cap in the locked position, each of the outwardly facing U-shaped receptacles having an inner surface thereof defining a stop by which the rotation of the protective cap relative to the applicator tip in the first direction for screwing on the protective cap after overrunning the at least one counter tooth is stopped.

20. A discharging device for a dispenser for discharging pharmaceutical liquids, said discharging device including:
   a housing having a coupling geometry for mounting on a liquid storage unit,
   an applicator tip having a discharge opening arranged on a distal end, and
   a protective cap,
   wherein
   the discharging device includes an actuation unit including the applicator tip which is displaceable in an axial direction in relation to the housing and has a finger support surface adapted to receive a user's finger, wherein liquid originating from the liquid storage unit can be output through the discharge opening into a surrounding atmosphere by the actuation unit,
   the actuation unit is mounted in the housing so as to be rotatable relative to the housing and displaceable in the axial direction,
   the applicator tip comprises an external thread and the protective cap comprises an internal thread which interacts with the external thread of the applicator tip,
   at least one locking tooth is provided on the protective cap and at least one counter tooth is provided on an upper side of the finger support surface of the applicator tip, wherein when the protective cap is rotated relative to the applicator tip in a first direction for screwing on the protective cap, the at least one locking tooth overruns the at least one counter tooth and, after overrunning, the at least one locking tooth and the at least one counter tooth prevent a rotation in a second direction opposite to the first direction for unscrewing the protective cap, and
   the protective cap is resiliently deformable at least in portions in order to disengage the at least one locking tooth and the at least one counter tooth as a result of resiliently deforming the protective cap.

21. The discharging device as claimed in claim 20, wherein the external thread extends over an angle of less than 180°.

22. The discharging device as claimed in claim 20, wherein the at least one locking tooth comprises a pair of opposite inwardly radially projecting locking teeth, and including a pair of opposite outwardly radially extending receptacle members provided on the upper side of the finger support surface of the applicator tip, each of the receptacle members having an outwardly facing U-shaped receptacle for receiving one of the locking teeth therein when the protective cap is in a locked position, an outer surface of the receptacle members defining the at least one counter tooth such that each of the locking teeth have to overrun the outer surface of the receptacle members and be received within the U-shaped receptacle for locking the cap in the locked position, each of the outwardly facing U-shaped receptacles having an inner surface thereof defining a stop by which the rotation of the protective cap relative to the applicator tip in the first direction for screwing on the protective cap after overrunning the at least one counter tooth is stopped.

* * * * *